US00RE49335E

(19) United States
(12) Reissued Patent
Zhou

(10) Patent Number: US RE49,335 E
(45) Date of Reissued Patent: Dec. 20, 2022

(54) ATOMIZER

(71) Applicant: md&c Creative Maison SA, Geneva (CH)

(72) Inventor: Xuewu Zhou, Shenzhen (CN)

(21) Appl. No.: 17/337,916

(22) Filed: Jun. 3, 2021

Related U.S. Patent Documents

Reissue of:
(64) Patent No.: 9,894,931
Issued: Feb. 20, 2018
Appl. No.: 13/985,700
Filed: Sep. 19, 2014

U.S. Applications:
(63) Continuation of application No. 16/787,424, filed as application No. PCT/CN2012/073089 on Mar. 27,
(Continued)

(30) Foreign Application Priority Data

Nov. 25, 2011 (CN) ..... 201120476199.7

(51) Int. Cl.
*A61M 15/02* (2006.01)
*A24F 40/485* (2020.01)
(Continued)

(52) U.S. Cl.
CPC ..... *A61M 15/02* (2013.01); *A24F 40/485* (2020.01); *A24F 40/50* (2020.01); *A61M 15/06* (2013.01);
(Continued)

(58) Field of Classification Search
CPC ..... A61M 15/02; A61M 15/06; A61M 2205/8206; A24F 40/485; A24F 40/50; A24F 40/10; A61N 1/44; H05B 3/03
See application file for complete search history.

(56) References Cited

U.S. PATENT DOCUMENTS 5,574,619 A * 11/1996 Jeong ..... H01T 23/00 361/213
5,654,866 A * 8/1997 Jeong ..... A61L 9/22 348/E5.128
(Continued)

FOREIGN PATENT DOCUMENTS

CN 201188868 Y 3/2009
CN 201393548 2/2010
(Continued)

OTHER PUBLICATIONS

"Non-Final Office Action", U.S. Appl. No. 16/787,424, United States Patent and Trademark Office, dated Sep. 24, 2021, 9 pgs.
(Continued)

*Primary Examiner* — Norca L. Torres Velazquez
(74) *Attorney, Agent, or Firm* — Erik G. Swenson; Carlson, Caspers, Vandenburgh & Lindquist, P.A.

(57) ABSTRACT

Provided is an anion electronic cigarette that includes an atomizer (1) and battery assembly (2) which are electrically connected to each other. The anionic electronic cigarette further includes an anion generation device, comprising an anion generator (14) which is electrically connected to the control circuit provided in the battery assembly (2). The anion electronic cigarette causes electronic smoke comprised of high-density anions to enter the human body, which can help smokers to mitigate the smoking addiction and even quit smoking, while providing a cleaner a method of smoking. At the same time, when it is required to add liquid tobacco tar into the electronic cigarette in the present
(Continued)

invention, it only requires opening the cigarette nozzle and pulling out the sealing pillar from the tar injection hole to inject tobacco tar into the tobacco tar cavity, which is fast and convenient and is not easy for tar to leak.

23 Claims, 6 Drawing Sheets

Related U.S. Application Data

2012, now Pat. No. Re. 49,160, which is an application for the reissue of Pat. No. 9,894,931.

(51) Int. Cl.

| | |
|---|---|
| ***A24F 40/50*** | (2020.01) |
| ***A61M 15/06*** | (2006.01) |
| ***H05B 3/03*** | (2006.01) |
| ***A24F 40/10*** | (2020.01) |
| ***A61N 1/44*** | (2006.01) |

(52) U.S. Cl.

CPC ..... *H05B 3/03* (2013.01); *A24F 40/10* (2020.01); *A61M 2205/8206* (2013.01); *A61N 1/44* (2013.01)

(56) References Cited

U.S. PATENT DOCUMENTS

| | | | | |
|---|---|---|---|---|
| 5,666,977 | A * | 9/1997 | Higgins | A24F 47/008 128/200.14 |
| 7,832,410 | B2 | 11/2010 | Hon | |
| 8,442,390 | B2 | 5/2013 | Nichols et al. | |
| 8,499,766 | B1 | 8/2013 | Newton | |
| 8,528,569 | B1 | 9/2013 | Newton | |
| 8,678,012 | B2 | 3/2014 | Li et al. | |
| 8,833,364 | B2 * | 9/2014 | Buchberger | A61M 11/041 128/200.14 |
| 9,022,026 | B2 | 5/2015 | Fang | |
| 2004/0047772 | A1 * | 3/2004 | Kwak | A61L 9/18 422/121 |
| 2006/0078460 | A1 * | 4/2006 | Ryu | A61L 9/12 422/5 |
| 2008/0156326 | A1 | 7/2008 | Belcastro et al. | |
| 2009/0095311 | A1 * | 4/2009 | Han | A24F 47/008 131/194 |
| 2009/0188490 | A1 | 7/2009 | Han | |
| 2009/0272379 | A1 | 11/2009 | Thorens et al. | |
| 2010/0200008 | A1 * | 8/2010 | Taieb | A24F 47/008 131/360 |
| 2010/0307518 | A1 * | 12/2010 | Wang | A24F 47/008 131/329 |
| 2011/0036346 | A1 | 2/2011 | Cohen et al. | |
| 2011/0277780 | A1 * | 11/2011 | Terry | A24F 47/008 131/273 |
| 2011/0303231 | A1 | 12/2011 | Li et al. | |
| 2012/0145169 | A1 | 6/2012 | Wu | |
| 2012/0279512 | A1 * | 11/2012 | Hon | A24F 47/008 131/329 |
| 2013/0192618 | A1 * | 8/2013 | Li | A24F 47/008 131/329 |
| 2013/0319438 | A1 * | 12/2013 | Liu | A24F 47/008 131/329 |
| 2013/0333711 | A1 * | 12/2013 | Liu | A24F 47/008 131/329 |
| 2014/0190501 | A1 * | 7/2014 | Liu | A24F 47/008 131/329 |
| 2014/0311503 | A1 * | 10/2014 | Liu | G02B 27/18 131/329 |
| 2015/0020826 | A1 * | 1/2015 | Liu | A24F 47/008 131/329 |
| 2015/0034104 | A1 * | 2/2015 | Zhou | A24F 47/008 131/329 |
| 2015/0144148 | A1 | 5/2015 | Chen | |
| 2015/0266032 | A1 * | 9/2015 | Zhou | B03C 3/0175 96/53 |
| 2015/0305410 | A1 * | 10/2015 | Liu | A24F 47/008 131/329 |
| 2016/0095357 | A1 * | 4/2016 | Burton | A24F 47/008 131/328 |
| 2016/0128385 | A1 * | 5/2016 | Lin | A24F 47/002 131/328 |
| 2016/0150827 | A1 * | 6/2016 | Liu | A24F 47/008 131/329 |
| 2016/0192708 | A1 * | 7/2016 | DeMeritt | H05B 3/40 131/329 |
| 2016/0192709 | A1 * | 7/2016 | Liu | H05B 3/40 131/329 |
| 2016/0338412 | A1 | 11/2016 | Monsees et al. | |
| 2017/0196272 | A1 * | 7/2017 | Li | A24F 47/008 |

FOREIGN PATENT DOCUMENTS

| | | | |
|---|---|---|---|
| CN | 201436037 | U | 4/2010 |
| CN | 101869356 | A | 10/2010 |
| CN | 201781984 | U | 4/2011 |
| CN | 102106611 | A | 6/2011 |
| CN | 201894185 | U | 7/2011 |
| CN | 201900065 | U | 7/2011 |
| CN | 102160906 | A | 8/2011 |
| CN | 202456410 | U | 10/2012 |
| EP | 2340729 | A1 | 7/2011 |
| JP | 2007-259840 | A | 10/2007 |
| KR | 200453400 | Y1 | 4/2011 |
| KR | 200453424 | Y1 | 5/2011 |
| KR | 20110006928 | U | 7/2011 |
| KR | 101081481 | B1 | 11/2011 |
| KR | 20110010862 | U | 11/2011 |
| WO | WO2006/021153 | A1 | 3/2006 |
| WO | 2010118644 | A1 | 10/2010 |

OTHER PUBLICATIONS

"Notice of Allowance and Fees Due", U.S. Appl. No. 16/787,424, United States Patent and Trademark Office, dated Jun. 7, 2022, 8 pgs.

"Examiner Interview Summary Record", U.S. Appl. No. 16/787,424, United States Patent and Trademark Office, dated Feb. 11, 2022, 3 pgs.

"Final Office Action", U.S. Appl. No. 16/787,424, United States Patent and Trademark Office, dated Jan. 12, 2022, 13 pgs.

International Search Report for PCT/CN2012/073089.

* cited by examiner

Amended

NEW

ATOMIZER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application [claims priority to patent applications: 1.)] *is an application for reissue of U.S. Pat. No. 9,894,931, and is a continuation of application Ser. No. 16/787,424, filed Feb. 11, 2020, which is also a reissue of U.S. Pat. No. 9,894,931, issued Feb. 20, 2018, which is a U.S. National Stage Entry of* Patent Cooperation Treaty Application *No.* PCT/CN2012/073089, filed Mar. [26] *27*, 2012 [and 2.)], *which claims priority to* Chinese Patent Application *No.* CN201120476199.7, filed Nov. 25, 2011. Each of the above cited applications *claims the benefit of the Nov. 25, 2011 priority date. Furthermore, each of the above cited applications* is hereby incorporated by reference herein as if fully set forth in [its] *their* entirety.

*More than one reissue application has been filed for the reissue of U.S. Pat. No. 9,894,931. The reissue applications are Ser. No. 17/337,916, and reissue application Ser. No. 16/787,424.*

TECHNICAL FIELD

The invention relates to an electronic cigarette, more particularly to [An] *an* anion electronic cigarette capable of generating a large number of anions and *to an improved atomizer* convenient for the addition of tobacco tar.

BACKGROUND

At present, it is well known that electronic cigarette consists of an atomizer and a battery assembly, the atomizer consists mainly of an atomizing chamber, a tobacco tar storage cup, a sealing cover, a steel tube shell and a holder, however, when liquid tobacco tar is added to the electronic cigarette having such a structure, the shell must be removed at first, and then the tobacco tar storage cup is taken off for adding the liquid tobacco tar, this way is extremely complex and liable to cause tobacco tar leakage, hence, its use is quite inconvenient.

Moreover, most of people who smoke electronic cigarettes smoked general cigarettes in the past, vast harmful substances have been deposited in their body, electronic cigarettes could not help these people quit smoking even if they are capable of replacing common cigarettes temporarily, as a result, further improvement on the function of electronic cigarettes is required.

SUMMARY OF THE INVENTION

In view of the defects in the prior art, *in a first aspect of* the invention [provides An anion electronic cigarette, the] *an* electronic cigarette is provided with an anion generator therein, so a large number of anions are inhaled by people who smoke the electronic cigarette, thus contributing to the removal of harmful substances in *the* human body and assisting *the* smoker in resisting smoke temptation and even quitting smoking. [Meanwhile] *In a second aspect of the invention*, [the] *an* improvement on the structure of the atomizer leads to more convenient addition of tobacco tar and low possibility of tobacco tar leakage.

In order to achieve the above objective, the invention adopts the technical proposal as follows:

An anion electronic cigarette comprises an atomizer and a battery assembly that are electrically connected with each other, and further comprises an anion generation device that comprises an anion generator and a control circuit, the anion generator is arranged on an electronic smoke flow channel and is electrically connected with the control circuit arranged inside the battery assembly.

[Wherein,] *The improvement on the structure of* the atomizer comprises:

an ergonomic holder, the holder is internally provided with a hollow cavity, a smoke guide sleeve is fixed in the hollow cavity in the holder, and the smoke guide sleeve is provided with sealing cylinders (41) extending downwards;

an upper sealing ring, the upper sealing ring is provided with an axial through hole, the upper plate surface of the upper sealing ring is provided with an annular protrusion which is coaxial with the through hole, the annular protrusion is in coaxial airtight fit with the lower end of the through hole of the smoke guide sleeve, injection holes are arranged on the outside plate surface of the annular protrusion, the injection holes are in fluid-tight fit with the sealing cylinders; and the side surface of the sealing ring is provided with a sealing gasket;

a smoke generation device, the smoke generation device consists of an atomizing cover, a tobacco tar guide rope, a heating wire and an atomizing cup, an integrated smoke guide tube is arranged on the upper end of the atomizing cover and is internally communicated with the cover, the atomizing cover is respectively provided with a groove at the two sides in the diameter direction; an annular protrusion is arranged on the middle-upper part of the atomizing cup, the wall of the atomizing cup is respectively provided, in the diameter direction, with grooves capable of holding the tobacco tar guide rope, the atomizing cup is sleeved, above the annular protrusion, into the atomizing cover to form an atomizing hollow cavity, the groove is corresponding to the groove in position, the tobacco tar guide rope passes through the heating wire and then is arranged in the groove and the end tip of the rope extends out of the atomizing hollow cavity; and the heating wire is electrically connected with the battery assembly (2);

a lower sealing ring, the sealing ring is provided with a through hole in fluid-tight fit with the lower end of the atomizing cup, a groove in fit with the annular protrusion of the atomizing cup is arranged on the upper end face of the sealing ring, and a sealing gasket is arranged at the outer side of the lower sealing ring;

a smoke guide tube, one end of the smoke guide tube is connected with the lower end of the through hole of the upper sealing ring in an airtight fit manner, and the other end is connected with the smoke guide tube on the upper end of the atomizing cover in an airtight fit manner and supports the upper sealing ring and the atomizing cover;

an atomizer shell, the upper end of the straight barrel-shaped atomizer shell is in fit connection with the holder; the upper sealing ring, the smoke guide tube, the smoke generation device and the lower sealing ring are accommodated in the hollow cavity inside the shell to form an electronic cigarette atomizer, the upper sealing ring and the lower sealing ring form an electronic cigarette tobacco tar cavity together with the hollow cavity inside the shell, and smoke inlet holes are arranged on the side surfaces of the lower end of the atomizer shell.

The anion generator is arranged on a smoke channel on the bottom of the electronic cigarette atomizer, and a smoke flow passes through the anion generator before entering the atomizer, so as to generate a large number of anions.

An annular protrusion is arranged outwards on the lower end of the smoke guide sleeve, the two sealing cylinders extending downwards are respectively arranged on a diameter line of the annular protrusion, and the upper sealing ring is provided with the injections holes that are corresponding to the two sealing cylinders in position and are in fluid-tight fit with the two sealing cylinders.

A mounting portion is arranged on the lower end of the atomizer shell and is sleeved with a decorative ring, the decorative ring is provided with smoke through holes corresponding to the smoke inlet holes, and two mounting bayonets are arranged on the two sides of the mounting portion and are used for the connection with the battery assembly.

The atomizing cup is made of a ceramic material.

The heating wire is connected with an electrode contact plate via a lead wire, and the electrode contact plate is provided with electrode contacts.

The electronic cigarette has a flat section.

The electronic cigarette further comprises a holder cover in fit with the holder.

Since the structure above is adopted, the anion generator is arranged in the electronic cigarette of the invention, high-concentration anions enter into human body through electronic smoke when people smoke the electronic cigarette, thus contributing to the removal of harmful substances in human body and assisting smoker in resisting smoke temptation and even quitting smoking. Meanwhile, when the addition of liquid tobacco tar is required, only the holder of the electronic cigarette of the invention needs to be opened and the sealing cylinders are pulled out of the injection holes so as to inject the tobacco tar into the tobacco tar cavity, which is convenient, fast, and difficult to cause tobacco tar leakage.

Figure 1:
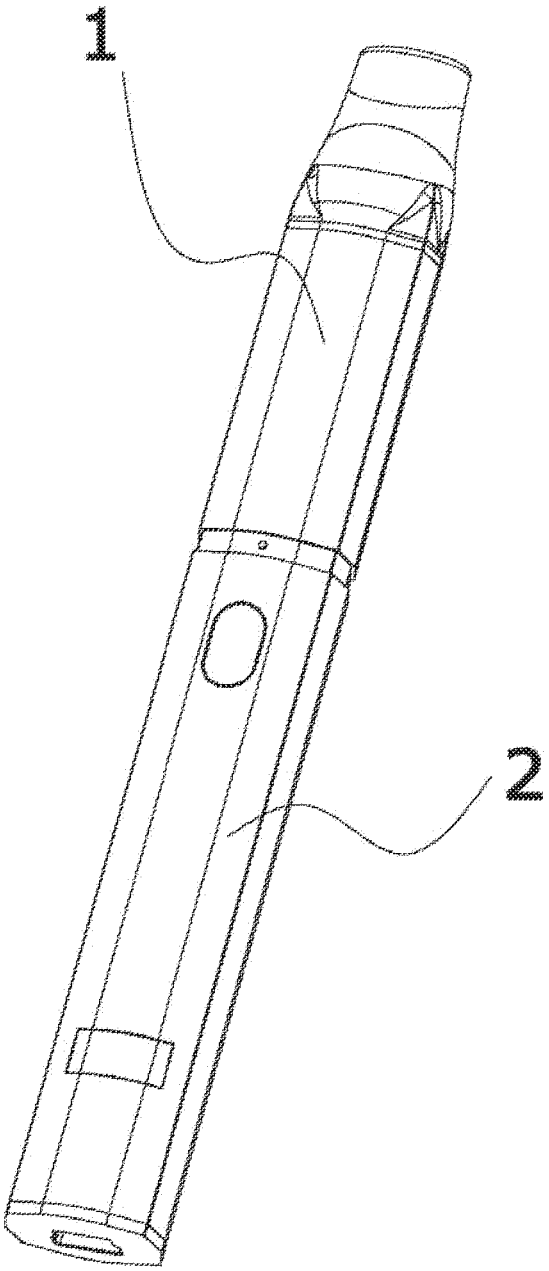
FIG. 1 is a structural schematic diagram of the invention.
Figure 2A:
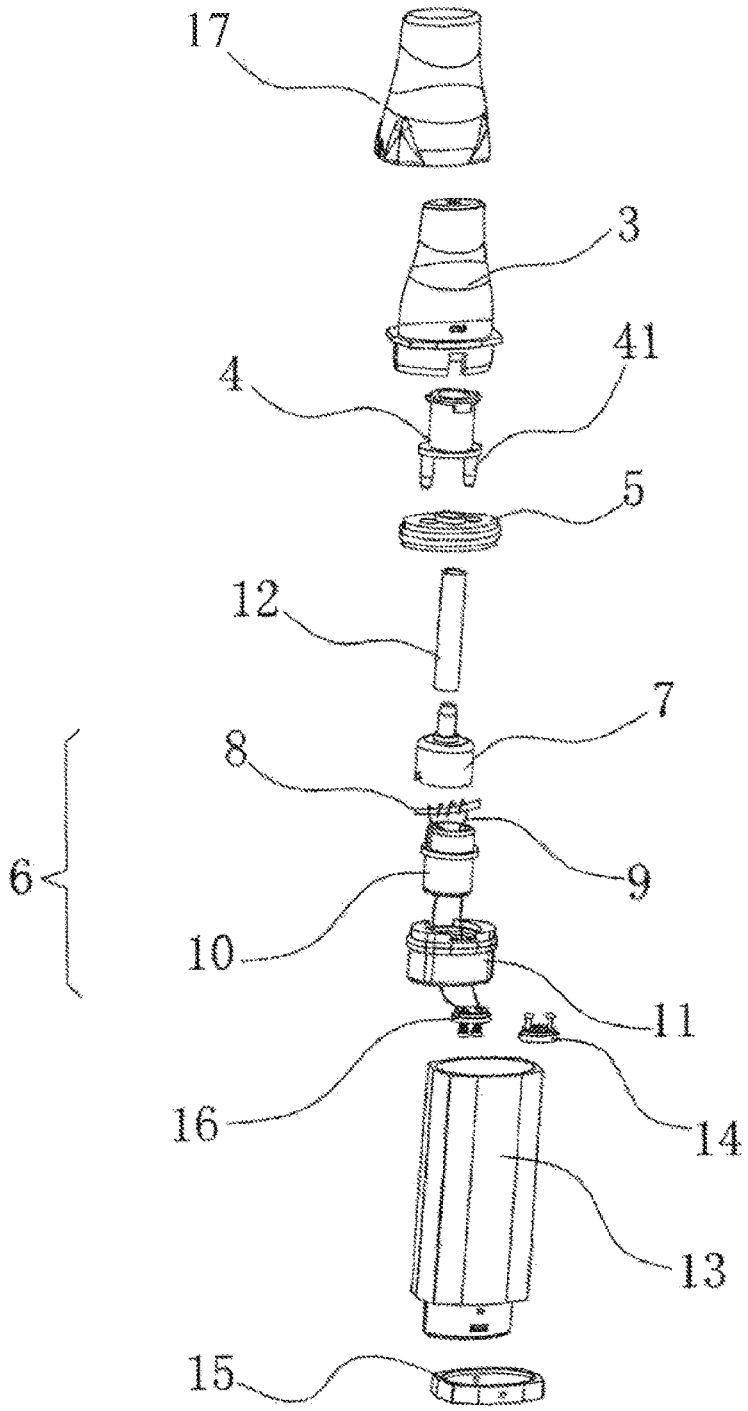
Figure 2B:
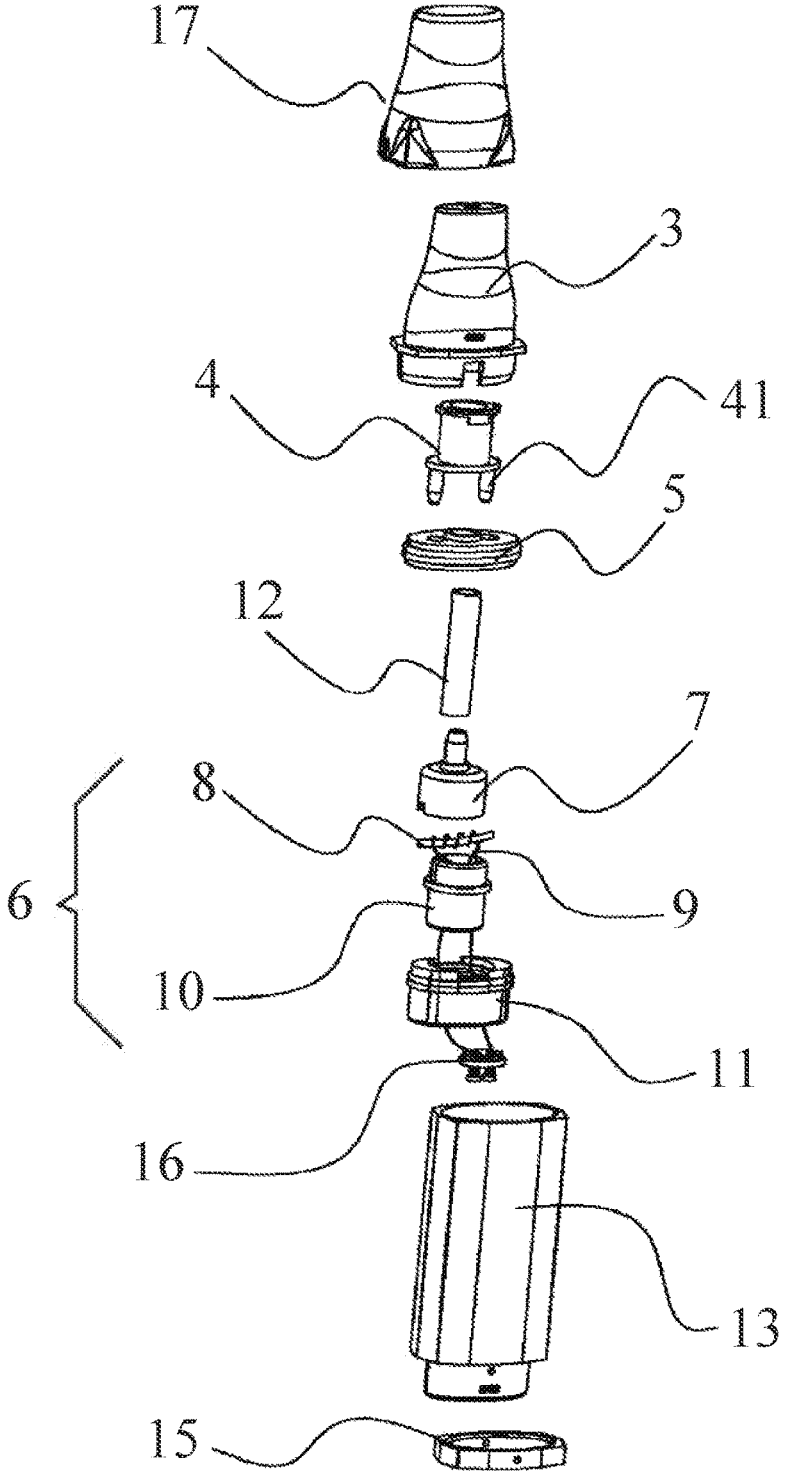

FIG. [2] *2A* is an exploded view of the smoke guide sleeve of FIG. 1, *according to a first example embodiment of the invention*;

*FIG. 2B is an exploded view of the smoke guide sleeve of FIG. 1, according to a second example embodiment of the invention;*

Figure 3:
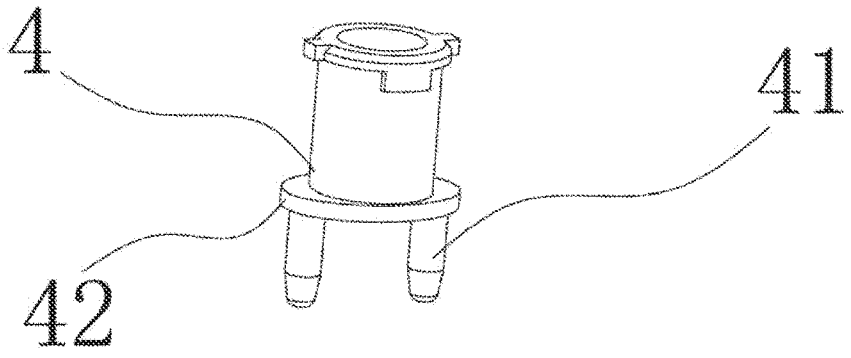
Figure 4:
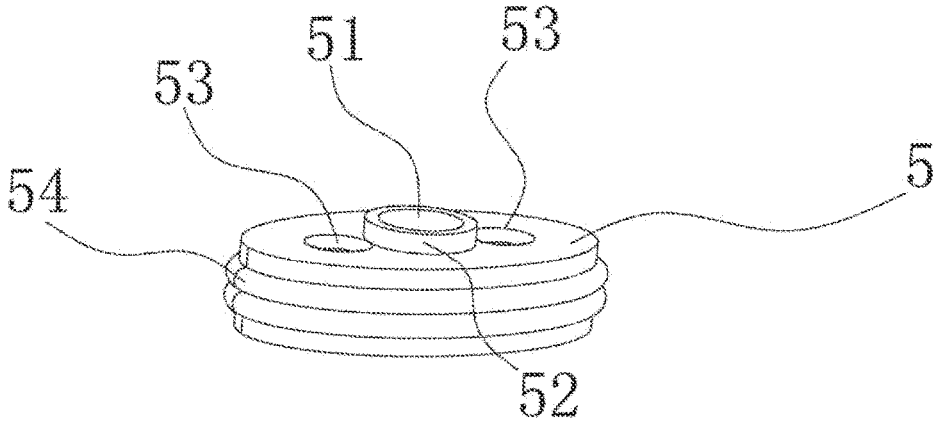
Figure 5:
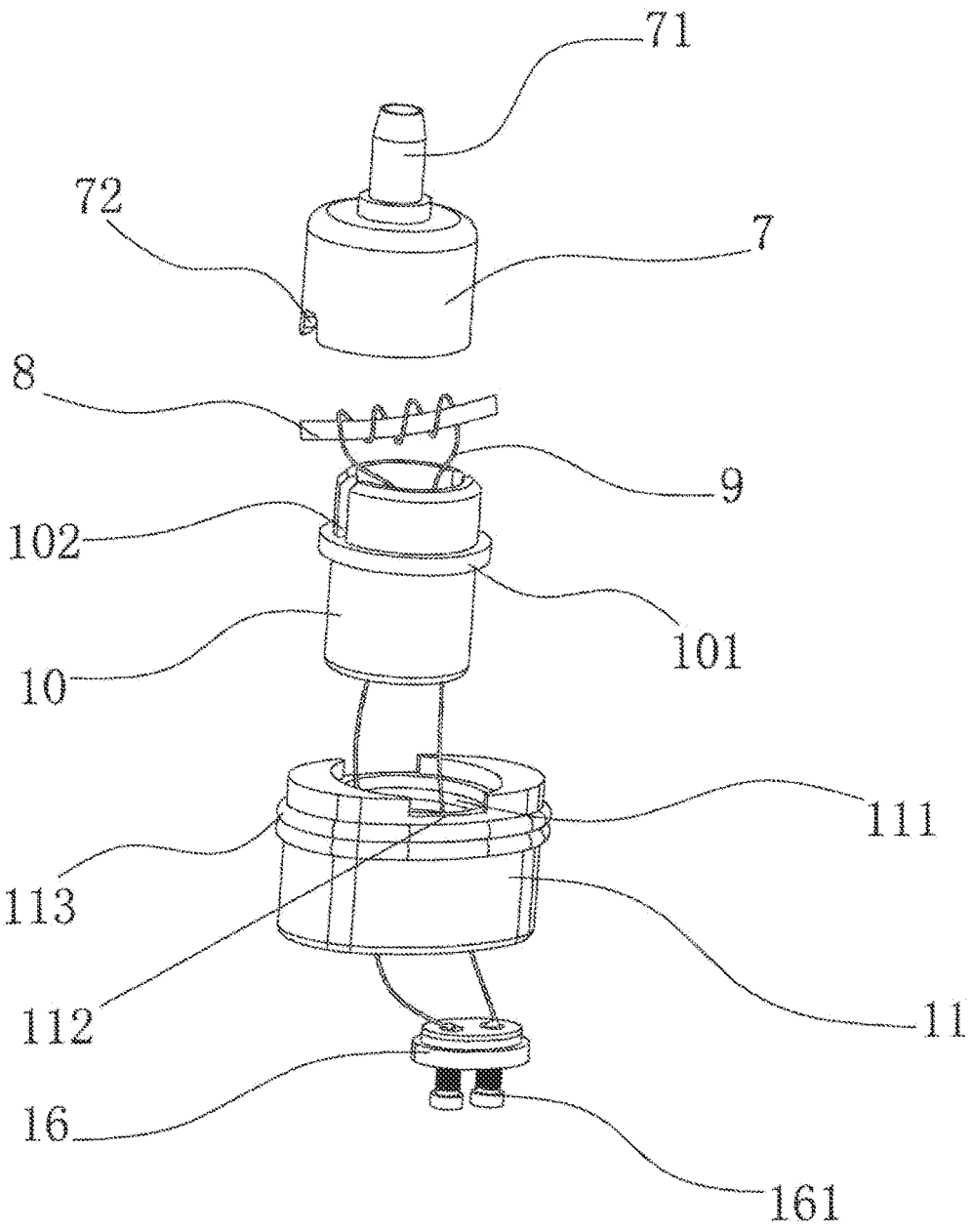
Figure 6:
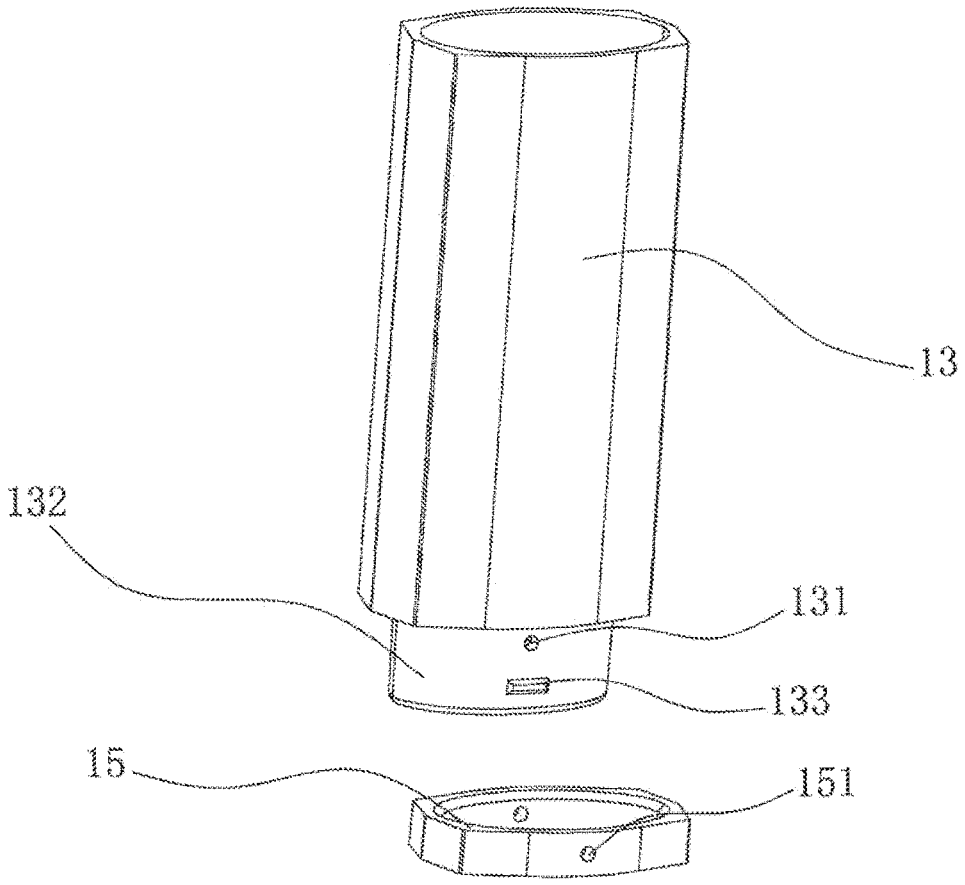

FIG. 3 is an enlarged view of the smoke guide sleeve of the invention;

FIG. 4 is an enlarged view of the upper sealing ring of the invention;

FIG. 5 is an enlarged view of the smoke generation device and the lower sealing ring of the invention;

FIG. 6 is an enlarged view of the atomizer shell of the invention.

DETAILED DESCRIPTION OF THE EMBODIMENTS

Detailed Description is made below to the invention with reference to the drawings and the embodiments.

Referring to FIG. 1 [and FIG. 2], [a negative] *an* electronic cigarette [of the invention] having a flat section comprises an atomizer 1 and a battery assembly 2 that are electrically connected with each other. [Meanwhile, the anion] *Referring to FIG. 2A, in a first embodiment of the present invention, the* electronic cigarette further comprises an anion generation device that comprises an anion generator 14 and a control circuit (not shown in the drawings), the anion generator 14 is arranged on an electronic smoke flow channel and is electrically connected with the control circuit arranged inside the battery assembly 2.

[Wherein,] *Referring to FIG. 2B, in a second embodiment of the present invention,* the atomizer comprises an ergonomic holder 3, an upper sealing ring 5, a smoke guide tube 12, a smoke generation device 6, a lower sealing ring 11 and an atomizer shell 13. *FIG. 2B differs from FIG. 2A in that the anion generator 14 of the first embodiment of FIG. 2A is not included in the second embodiment of FIG. 2B.*

The atomizer shell 13 is internally provided with a hollow cavity, a smoke guide sleeve 4 is fixed in the hollow cavity in the holder 3, an annular protrusion 42 is arranged outwards on the lower end of the smoke guide sleeve 4, and two sealing cylinders 41 extending downwards are respectively arranged on a diameter line of the annular protrusion 42. (Referring to FIG. 3)

The upper sealing ring 5 is provided with an axial through hole 5, the upper plate surface of the upper sealing ring 5 is provided with an annular protrusion 52 which is coaxial with the through hole 51, the annular protrusion 52 is in coaxial airtight fit with the lower end of the through hole of the smoke guide sleeve 4, two injection holes 53 are arranged on the outside plate surface of the annular protrusion 52, the injection holes 53 are in fluid-tight fit with the sealing cylinders 41; and the side surface of the sealing ring 5 is provided with a sealing gasket 54. (Referring to FIG. 4)

The smoke generation device 6 consists of an atomizing cover 7, a tobacco tar guide rope 8, a heating wire 9 and an atomizing cup 10, an integrated smoke guide tube 71 is arranged on the upper end of the atomizing cover 7 and is internally communicated with the cover, the atomizing cover 7 is respectively provided with a groove 72 at the two sides in the diameter direction. An annular protrusion 101 is arranged on the middle-upper part of the atomizing cup 10 which is made of a ceramic material, the wall of the atomizing cup 10 is respectively provided, in the diameter direction, with grooves 102 capable of holding the tobacco tar guide rope 8, the atomizing cup 10 is sleeved, above the annular protrusion 101, into the atomizing cover 7 to form an atomizing hollow cavity, the groove 72 is corresponding to the groove 102 in position. The tobacco tar guide rope 8 passes through the heating wire 9 and then is arranged in the groove 102 and the end tip of the rope extends out of the atomizing hollow cavity. The heating wire 9 is connected with an electrode contact plate 16 via a lead wire, the electrode contact plate is provided with electrode contacts 161, and the electrode contacts 161 are electrically connected with the battery assembly 2. (Referring to FIG. 5)

The lower sealing ring 11 is provided with a through hole 111 in fluid-tight fit with the lower end of the atomizing cup 10, a groove 112 in fit with the annular protrusion 101 of the atomizing cup 10 is arranged on the upper end face of the sealing ring, and a sealing gasket 113 is arranged at the outer side of the lower sealing ring 11. (Referring to FIG. 5)

One end of the smoke guide tube 12 is connected with the lower end of the through hole 51 of the upper sealing ring 5 in an airtight fit manner, and the other end is connected with the smoke guide tube 71 on the upper end of the atomizing cover 7 in an airtight fit manner and supports the upper sealing ring 5 and the atomizing cover 7.

The upper end of the straight barrel-shaped atomizer shell 13 is in fit connection with the holder 3; the upper sealing ring 5, the smoke guide tube 12, the smoke generation device 6 and the lower sealing ring 11 are accommodated in the hollow cavity inside the shell to form an electronic cigarette atomizer, and the upper sealing ring 5 and the lower sealing ring 11 form an electronic cigarette tobacco tar cavity together with the hollow cavity inside the shell. A mounting portion 132 is arranged on the lower end of the atomizer shell 13, the mounting portion 132 is provided with two smoke inlet holes 131 and is sleeved with a decorative ring 15, the decorative ring 15 is provided with smoke through holes 151 corresponding to the smoke inlet holes 131, and two mounting bayonets 133 are arranged on the two sides of the mounting portion and are used for the clamped connection with the battery assembly.

The embodiments discussed above are merely for describing the invention better and are not intended to limit the scope of the invention, therefore, slight changes and equivalent variations made without departing from the spirit of this patent shall be contemplated as being within the scope of the invention.

The invention claimed is:

[1. An anion electronic cigarette, comprising an atomizer (1) and a battery assembly (2) that are electrically connected with each other, characterized in that: the anion electronic cigarette further comprises an anion generation device that comprises an anion generator (14) and a control circuit, the generator (14) is arranged on an electronic smoke flow channel, wherein the atomizer (1) comprises:

an ergonomic holder (3), the holder (3) being internally provided with a hollow cavity, a smoke guide sleeve (4) being fixed in the hollow cavity in the holder (3), and the smoke guide sleeve (4) being provided with sealing cylinders (41) extending downwards;

an upper sealing ring (5), the upper sealing ring (5) being provided with an axial through hole (51), the upper plate surface of the upper sealing ring (5) being provided with an annular protrusion (52) which is coaxial with the though hole (51), the annular protrusion (52) being in coaxial airtight fit with the lower end of the through hole of the smoke guide sleeve (4), injection holes (53) being arranged on the outside plate surface of the annular protrusion (52), the injection boles (53) being in fluid-tight fit with the sealing cylinders (41); and the side surface of the sealing ring (5) being provided with a sealing gasket (54);

an smoke generation device (6), the smoke generation device (6) consisting of an atomizing cover (7), a tobacco tar guide rope (8), a heating wire (9) and an atomizing cup (10), an integrated smoke guide tube (71) being arranged on the upper end of the atomizing cover (7) and being internally communicated with the cover, the atomizing cover (7) being respectively provided with a groove (72) at the two sides in the diameter direction; and annular protrusion (101) being arranged on the middle-upper part of the atomizing cup (10), the wall of the atomizing cup (10) being respectively provided, in the diameter direction, with groves (102) capable of holding the tobacco tar guide rope (8), the atomizing cup (10) being sleeved, above the annular protrusion (101), into the atomizing cover (7) to form an atomizing hollow cavity, the groove (72) being corresponding to the groove (102) in position, the tobacco tar guide rope (8) passing, through the heating wire (9) and then being arranged in the groove (102) and the end tip of the rope extending out of the atomizing hollow cavity; and the heating wire (9) being electrically connected with the battery assembly (2);

a lower sealing ring (11), the sealing ring (11) being provided with a through hole (111) in fluid-tight fit with the lower end of the atomizing cup (10, a groove (112) in fit with the annular protrusion (101) of the atomizing cup (10) being arranged on the upper end face of the sealing ring, and a sealing gasket (113) being arranged at the outer side of the lower sealing ring (11);

a smoke guide tube (12), one end of the smoke guide tube (12) being connected with the lower end of the through hole (51) of the upper sealing ring (5) in an airtight fit manner, and the other end being connected with the smoke guide tube (71) on the upper end of the atomizing cover (7) in an airtight fit manner and supporting the upper sealing ring (5) and the atomizing cover (7);

an atomizer shell (13), the upper end of the straight barrel-shaped atomizer shell (13) being in fit connection with the holder (3); the upper sealing ring (5), the smoke guide tube (12), the smoke generation device (6) and the lower sealing ring (11) being accommodated in the hollow cavity inside the shell to form an electronic cigarette tobacco tar cavity together with the hollow cavity inside the shell, and smoke inlet holes (131) being arranged on the side surfaces of the lower end of the atomizer shell (13).]

[2. The anion electronic cigarette according to claim 1, characterized in that the anion generator (14) is arranged on a smoke channel on the bottom of the electronic cigarette atomizer, and a smoke flow passes through the anion generator (14) before entering the atomizer, so as to generate a large number of anions.]

[3. The anion electronic cigarette according to claim 1, characterized in that an annular protrusion (42) is arranged outwards on the lower end of the smoke guide sleeve (4), the two sealing cylinders (41) extending downwards are respectively arranged on a diameter line of the annular protrusion (42), and the upper sealing ring (5) is provided with the injection holes (53) that are corresponding to the two sealing cylinders (41) in position and are in fluid-tight fit with the two sealing cylinders (41).]

[4. The anion electronic cigarette according to claim 1, characterized in that a mounting portion (132) in arranged on the lower end of the atomizer shell (13) and is sleeved with a decorative ring (15), the decorative ring (15) is provided with smoke through holes (151) corresponding to the smoke inlet holes (131), and two mounting bayonets (133) are arranged on the two sides of the mounting portion and are used for the connection with the battery assembly (2).]

[5. The anion electronic cigarette according to claim 1, characterized in that the atomizing cup (10) is made of a ceramic material.]

[6. The anion electronic cigarette according to claim 1, characterized in that the heating wire (9) is connected with an electrode contact plate (16) via a lead wire, and the electrode contact plate is provided with electrode contacts (161).]

[7. The anion electronic cigarette according to claim 1, characterized in that the electronic cigarette has a flat section.]

[8. The anion electronic cigarette according to claim 1, characterized in that the electronic cigarette further comprises a holder cover in fit with the holder.]

*9. An atomizer that is configured to be connected to a battery assembly of an electronic cigarette, the atomizer comprising:*

*a shell having a proximal portion for supporting a mouthpiece, and a distal portion including at least two mounting members for releasably connecting the atomizer to the battery assembly with a clamp connection, the shell including an atomizing cavity and further including a liquid cavity having a proximal end and a distal end;*

*a sealing member arranged inside the shell to seal the proximal end of the liquid cavity, the sealing member including a through hole for receiving a smoke guide tube;*

*a guide rope arranged in the atomizing cavity and passing through a heating wire therein; and*

*a cover that forms at least a portion of the atomizing cavity, the cover including an opening protrusion extending from an upper portion of the cover and two grooves formed on opposing sides of the cover, at least one end tip of the guide rope extending through at least one of the two grooves,*

*wherein the smoke guide tube is releasably connected to the opening protrusion of the cover in an airtight fit.*

*10. The atomizer according to claim 9, wherein the sealing member further includes a side surface with a protruding sealing gasket in contact with an inner surface of the shell and wherein the smoke guide tube extends in a coaxial direction through the through hole of the sealing member and toward the mouthpiece.*

*11. The atomizer according to claim 9, wherein the mouthpiece is operatively attachable to the proximal portion of the shell.*

*12. The atomizer according to claim 9, wherein the heating wire is electrically connected to electrical contacts.*

*13. The atomizer according to claim 12, wherein the electrical contacts are configured to electrically connect to the battery assembly when the atomizer and battery assembly are held in clamp connection with one another.*

*14. The atomizer according to claim 12, wherein the electrical contacts face distally, away from the mouthpiece.*

*15. The atomizer according to claim 9, wherein the guide rope is arranged to be perpendicular to an axis of longitudinal extension of the atomizer.*

*16. The atomizer according to claim 9, further comprising a guide located in the mouthpiece, the guide including a protrusion extending distally away from the mouthpiece.*

*17. The atomizer according to claim 16, wherein the sealing member includes a recess arranged next to the through hole, the recess configured to receive a portion of the protrusion.*

*18. The atomizer according to claim 17, further comprising at least one contact plate including the electrical contacts.*

*19. The atomizer according to claim 18, wherein the electrical contacts are on a surface of the at least one contact plate that is perpendicular to a center axis of the smoke guide tube.*

*20. The atomizer according to claim 9, further comprising a holder arranged in the shell, the holder including two openings aligned in a diameter direction with the two grooves of the cover.*

*21. An atomizer that is configured to be connected to a battery assembly of an electronic cigarette, the atomizer comprising:*

*a shell having a proximal portion for supporting a mouthpiece, and a distal portion including at least two mounting members for releasably connecting the atomizer to the battery assembly with a clamp connection, the shell including an atomizing cavity and further including a liquid cavity having a proximal end and a distal end;*

*a sealing member arranged inside the shell to seal the proximal end of the liquid cavity, the sealing member including a through hole for receiving a smoke guide tube;*

*a guide rope arranged in the atomizing cavity and passing through a heating wire therein; and*

*a cover and a holder configured to engage with each other to form at least a portion of the atomizing cavity, the cover including a first groove, the holder including a second groove, the guide rope arranged to extend out of the atomizing cavity through an opening formed by the first groove and the second groove,*

*wherein the smoke guide tube is releasably connected to the opening protrusion of the cover in an airtight fit.*

*22. The atomizer according to claim 21, wherein the sealing member further includes a side surface with a protruding sealing gasket in contact with an inner surface of the shell and wherein the smoke guide tube extends along the shell in a coaxial direction through the through hole of the sealing member and toward the mouthpiece.*

*23. The atomizer according to claim 21, wherein the mouthpiece is operatively attachable to the proximal portion of the shell.*

*24. The atomizer according to claim 21, wherein the heating wire is electrically connected to electrical contacts.*

*25. The atomizer according to claim 24, wherein the electrical contacts are configured to electrically connect to the battery assembly when the atomizer and battery assembly are held in clamp connection with one another.*

*26. The atomizer according to claim 24, wherein the electrical contacts face distally, away from the mouthpiece.*

*27. The atomizer according to claim 21, wherein the guide rope is arranged to be perpendicular to an axis of longitudinal extension of the atomizer.*

*28. The atomizer according to claim 21, further comprising a guide located in the mouthpiece, the guide including a protrusion extending distally away from the mouthpiece.*

*29. The atomizer according to claim 28, wherein the sealing member includes a recess arranged next to the through hole, the recess configured to receive a portion of the protrusion.*

*30. The atomizer according to 29, further comprising at least one contact plate including the electrical contacts.*

*31. The atomizer according to claim 30, wherein the electrical contacts are on a surface of the at least one contact plate that is perpendicular to a center axis of the smoke guide tube.*

* * * * *